United States Patent
Wijbrans et al.

(10) Patent No.: US 9,952,099 B2
(45) Date of Patent: Apr. 24, 2018

(54) TUNABLE FILTERS FOR SPECTRAL SENSING

(71) Applicant: KONINKLIJKE PHILIPS N.V., Eindhoven (NL)

(72) Inventors: Klaas Cornelis Jan Wijbrans, Eindhoven (NL); Gerhardus Wilhelmus Lucassen, Eindhoven (NL); Bernardus Hendrikus Wilhelmus Hendriks, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/664,336

(22) Filed: Jul. 31, 2017

(65) Prior Publication Data

US 2017/0328772 A1    Nov. 16, 2017

Related U.S. Application Data

(63) Continuation of application No. 15/125,686, filed as application No. PCT/EP2015/055251 on Mar. 13, 2015, now Pat. No. 9,719,854.

(30) Foreign Application Priority Data

Mar. 18, 2014 (EP) .................................. 14160522
Jul. 23, 2014 (EP) .................................. 14178156

(51) Int. Cl.
*G01J 3/00* (2006.01)
*G01J 3/12* (2006.01)
(Continued)

(52) U.S. Cl.
CPC .............. *G01J 3/12* (2013.01); *A61B 5/0075* (2013.01); *A61B 5/725* (2013.01); *A61B 5/7264* (2013.01);
(Continued)

(58) Field of Classification Search
CPC ..... A61B 5/0075; A61B 5/725; A61B 5/7264; G01J 2003/1213; G01J 3/12; G01J 3/26;
(Continued)

(56) References Cited

U.S. PATENT DOCUMENTS 5,022,730 A * 6/1991 Cimini .................... G02F 1/225
                                                         385/122
6,901,178 B2  5/2005 Bernasconi
(Continued)

FOREIGN PATENT DOCUMENTS

WO    2004057284 A1    7/2004
WO    2006114773 A1    11/2006
(Continued)

OTHER PUBLICATIONS

Meijerink, A. et al "Novel Ring Resonator-Based Integrated Photonic Beamformer for Broadband Phased Array Receive Antennas—Part I: Design and Performance Analysis", Journal of Lightwave Technology, vol. 28, No. 1, 2010, pp. 3-18. Abstract Only.

(Continued)

*Primary Examiner* — Sunghee Y Gray

(57) ABSTRACT

A spectroscopic analysis device for analysis of a sample comprises an input for receiving light from the sample and a photonic integrated circuit. This photonic optical filter comprises one or more tunable bandpass filters arranged to filter the received light. Furthermore, the device comprises a controller that is arranged—to control the one or more tunable bandpass filters, to receive filter results obtained from the one or more tunable bandpass filters, and to provide spectroscopic analysis results based on the received filter results.

6 Claims, 1 Drawing Sheet

(51) Int. Cl.
*G01J 3/26* (2006.01)
*G01J 3/28* (2006.01)
*G01N 21/25* (2006.01)
*G01N 21/31* (2006.01)
*G01N 21/47* (2006.01)
*G01N 21/49* (2006.01)
*A61B 5/00* (2006.01)

(52) U.S. Cl.
CPC . *G01J 3/26* (2013.01); *G01J 3/28* (2013.01); *G01N 21/255* (2013.01); *G01N 21/31* (2013.01); *G01N 21/474* (2013.01); *G01N 21/49* (2013.01); *G01J 2003/1213* (2013.01); *G01N 2201/12* (2013.01)

(58) Field of Classification Search
CPC ......... G01J 3/28; G01N 21/255; G01N 21/31; G01N 21/474; G01N 21/49; G01N 2201/12
USPC ........................................................ 356/300
See application file for complete search history.

(56) References Cited

U.S. PATENT DOCUMENTS

| | | | |
|---|---|---|---|
| 7,257,288 | B1 | 8/2007 | Strasser |
| 2001/0046363 | A1 | 11/2001 | Purchase |
| 2006/0132787 | A1 | 6/2006 | Mestha |
| 2007/0066877 | A1 | 3/2007 | Arnold |
| 2007/0109550 | A1 | 5/2007 | Ja |
| 2009/0245796 | A1 | 10/2009 | Little |
| 2011/0080581 | A1 | 4/2011 | Bhargava |
| 2012/0226118 | A1 | 9/2012 | Delbeke |

FOREIGN PATENT DOCUMENTS

| | | |
|---|---|---|
| WO | 2011132128 A1 | 10/2011 |
| WO | 2012093309 A1 | 7/2012 |
| WO | 2012127378 A1 | 9/2012 |
| WO | 2013001423 A1 | 1/2013 |

OTHER PUBLICATIONS

Roeloffzen et al "Silicon Nitride Microwave Photonic Circuits", Optics Express 22937, vol. 21, No. 19, 2013.

Muller, Manfred et al "Recovering intrinsic fluorescence by Monte Carlo modeling", Journal of Biomedical Optics, vol. 18 (2013) pp. 027009-1 to 027009-13.

Nachabe, Rami et al "Diagnosis of breast cancer using optical spectroscopy from 500 to 1600 nm: a comparison of classification methods", Journal of Biomedical Optics, vol. 16 (2011) p. 087010-1 to 087010-12.

Nachabe, Rami et al "Estimation of lipid and water concentrations in scattering media with diffuse optical spectroscopy from 900 to 1600 nm," Journal of Biomedical Optics, vol. 15, May 2010, pp. 037015-1 to 337015-10.

Nachabe, Rami et al "Estimation of biological chromophores using diffuse optical spectroscopy : benefit of extending the UV-VIS wavelength range to include 1000 to 1600 nm," Optics Express, vol. 18, 2010, pp. 879-888.

Farrel, Thomas J. et al "A diffusion theory model of spatially resolved, steady-state diffuse reflectance for the non-invasive determination of tissue optical properties," Med. Phys. 19 (1992) p. 879-888—Abstract Only.

Spliethoff, Jarich W. et al "Improved identification of peripheral lung tumors by using diffuse reflectance and fluorescence spectroscopy", Lung Cancer, vol. 80, Issue 2, 2013, p. 165-171—Abstract Only.

Evers, Daniel J. et al "Diffuse reflectance spectroscopy: A new tool for improvement of biopsy procedures in lung malignancies", Clinical Lung Cancer, vol. 13, Issue 6, 2012, pp. 424-431—Abstract Only.

* cited by examiner

TUNABLE FILTERS FOR SPECTRAL SENSING

CROSS REFERENCE TO PRIOR APPLICATIONS

This application is a Continuation of U.S. Ser. No. 15/125,686, filed Sep. 13, 2016, which is the U.S. National Phase application under 35 U.S.C. § 371 of International Application No. PCT/EP2015/055251, filed on Mar. 13, 2015, which claims the benefit of European Patent Application No. 14160522.0, filed on Mar. 18, 2014 and European Patent Application No. 14178156.7, filed on Jul. 23, 2014. These applications are hereby incorporated by reference herein.

FIELD OF THE INVENTION

The invention relates to a spectroscopic analysis device for analysis of a sample based on light received from the sample. Furthermore, the invention relates to the spectroscopic analysis and characterization of tissue.

BACKGROUND OF THE INVENTION

Devices for spectral tissue sensing and for other spectral sensing methods include a broadband light source and one or more broadband spectrometers. In practice, two of these are included because of the need to cover both the visible and the near infrared wavelength ranges. Example prior art for Spectral Tissue Sensing are disclosed in International Patent Applications WO2012/127378, WO2012/093309 and WO2013/001423. International Patent Application WO2011/132128 discloses an example where a limited number of wavelengths are used to detect water and lipid.

This Spectral Tissue Sensing has a great potential in many application areas, especially in the medical applications area. However, to become a success, both cost and form factor are of high importance. Current state of the art technology still requires systems that need to be transported on a separate cart and that involve high cost. The result is that these systems are only used in a hospital environment, where only a limited number of such devices will fit in the budget and workflow.

Document US20120226118A1 discloses an implantable sensor for sensing a substance such as glucose. The sensor comprises a photonic integrated circuit based radiation processor for spectrally processing radiation interacting with the sample.

Document US20070109550A1 discloses a system and method for detecting the optical spectrum of an optical input signal. The system includes a tunable optical filter having a microresonator that is tunable across a plurality of states and a processor. The input signal is coupled into the microresonator, which is continuously tuned across a spectral range that is narrow relative to the targeted detection range.

Document US2009/0245796 relates to the optical communications field and discloses a planar lightwave circuit that includes a substrate, a tunable filter, a demultiplexer, and an optical processor each disposed on the substrate. The tunable filter is configured to filter at least one of a bandwidth or a wavelength of a Wavelength Division Multiplexed optical input signal. The demultiplexer is connected to the tunable filter and configured to receive a filtered Wavelength Division Multiplexed optical input signal at an input and to supply one of a plurality of channels of the filtered Wavelength Division Multiplexed input signal at a respective one of a plurality of outputs. Each of the plurality of channels corresponds to one of a plurality of wavelengths of the filtered Wavelength Division Multiplexed input signal. The optical processor includes a bit-delay interferometer communicating with a respective one of the plurality of outputs of the demultiplexer. The optical processor is configured to receive one of the plurality of channels from the demultiplexer and output a plurality of demodulated optical signal components.

SUMMARY OF THE INVENTION

It is an object of the present invention to provide a spectroscopic analysis system that mitigates one or more of the problems related to the current systems. To this end, the invention provides a spectroscopic analysis device for analysis of a sample comprising: an input for receiving light from the sample, a photonic integrated circuit comprising one or more tunable bandpass filters arranged to filter the received light, and a controller arranged to control the one or more tunable bandpass filters, to receive filter results obtained from the one or more tunable bandpass filters, and to provide spectroscopic analysis results based on the received filter results.

An important element of the invention is the combination of fast detection and high resolution through tunable filters (for example resonators) on a photonic integrated circuit (PIC) with small broadband light source and a simple microcontroller. Fast detection is achieved because a limited number of wavelengths is measured simultaneously in a very narrow band per measurement. As a result of this, simple, low noise photo detectors can be used meaning that the dominant noise contribution is only the shot noise of the incoming light. To achieve a sufficient SNR of 40, only 1600 photons are needed meaning extremely fast measurement times. By combining fast tunable optical filters with appropriate classification algorithms, currently known diagnostic devices based on conventional spectroscopy are great improved, for example for tissue recognition.

According to the invention, both the form factor and cost can be reduced significantly, enabling application for mobile devices. This will not only broaden the application in the hospital, but also enables point of care application, and mobile or emergency services use. The capability of fast tuning (milliseconds) and high resolution (<0.1 nm) combined with sensitive photo detector and small size of the filter, allow for the integration of a bank of filters on a single chip that is fed from a single input signal.

Various types of tunable filters exist such as Fabry-Perot filters, acousto-optical tunable filters, Distributed Bragg Reflector optical filters (disclosed for example in U.S. Pat. No. 5,022,730), MEMS tunable filters (e.g. of DiCon Fiberoptics Inc http://www.diconfiberoptics.com/products/tunable_optical_filter.php) or tunable filters based on multivariate optical elements, as for example disclosed in International Patent Applications WO2004/057284, WO2006/114773. These known filters are either not sufficiently small to allow for the creation of a small spectroscopic analysis device, or suffer from a too small tuning range or have other disadvantages.

Fast tunable optical filters are known in the domain of telecommunications, see for example U.S. Pat. No. 6,901,178. With the advent of photonic integrated circuits, the creation of such filters at a low cost is now feasible on a substrate. In addition, the small size of the filter results in low time constants allowing for faster tuning. Such filters can be combined into more complex circuits, such as for example shown in the article of A. Meijerink et al., "Novel ring resonator-based integrated photonic beamformer for broadband phased array receive antennas—part I: design and performance analysis", Journal of Lightwave Technology, 2010, 28 (1). pp. 3-18. ISSN 0733-8724 and are therefore regarded of interest for application in the telecommunications area.

DETAILED DESCRIPTION OF EMBODIMENTS

Figure 1:
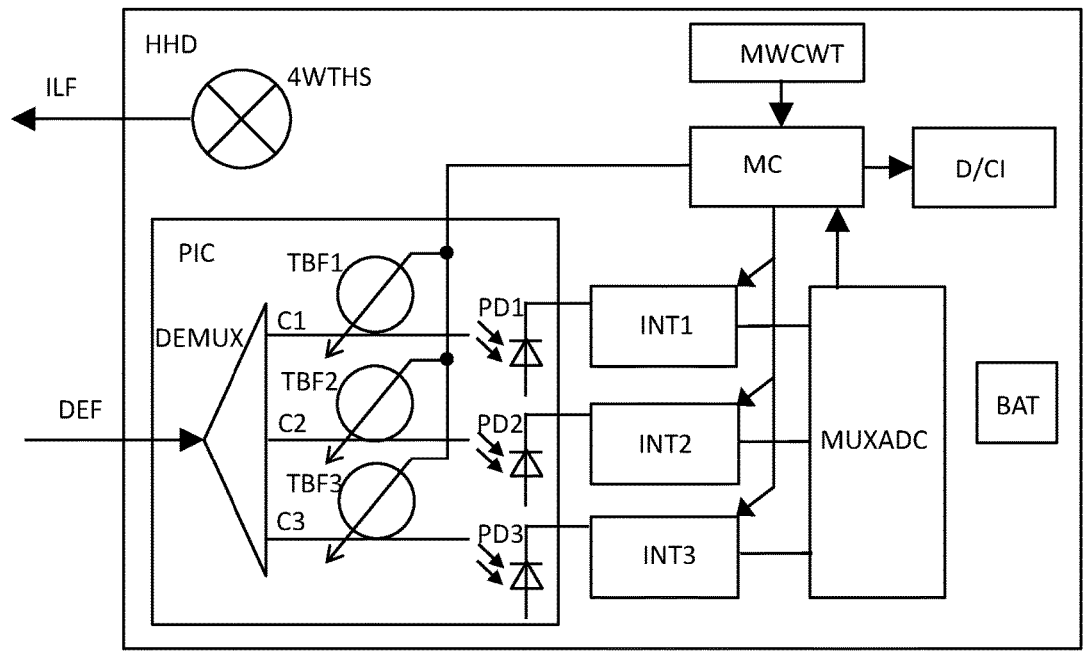
FIG. 1 shows an embodiment of the device according to the invention.

FIG. 1 shows an embodiment combining a light source (e.g. tungsten halogen exemplified by a 4 W Tungsten Halogen light source 4WTHS, LED or laser) with a photonic integrated circuit PIC containing a beam splitter (for example an arrayed waveguide grating (AWG)) and a number of tunable filters (consisting of for example ring cavity resonators), a photo detector per tunable filter output, an electronic integration circuit INT1 . . . INT3 for integrating the photo detector output over time, a multiplexing AD converter MUXADC and a microcontroller MC having a memory MWCWT (Memory with Coefficients and Wavelengths Table) configured to store the relevant wavelength ranges and corresponding spectral coefficients. A battery BAT for powering the device so that it can be used as a handheld device HHD is also illustrated in FIG. 1. To output the data, the device can be equipped with its own display, or controlled via for example a smartphone, smart watch or tablet computer using for example Bluetooth. This functionality is exemplified by Display or Communications Interface D/CI in FIG. 1. The tuning is dependent on the type of ring resonator used, and can for example be thermal, by tuning an optical delay line or by for example the electro-optical, thermo optical or acousto-optical changing of a refractive index. See for example the article by Roeloffzen et al, "Silicon Nitride microwave photonic circuits", OPTICS EXPRESS 22937, Vol. 21(19), 2013].

In operation, the micro controller MC activates the broadband light source 4WTHS. As a result, broadband light is output through the illumination fiber ILF to the optical probe towards the sample/object of interest. The object of interest scatters and absorbs parts of the light. A part of the scatter light is captured by the detection fiber DEF.

The incoming light from the detection fiber is offered over the whole wavelength range of interest (e.g., 400-2000 nm in the visible and near infra-red range that is currently used) to the PIC. The beam splitter (e.g., an AWG) distributes the incoming light over multiple tunable filters, each with its own wavelength tuning range. The tunable filter is a sharp bandpass filter, passing the light over a range of for example 0.1-5 nm. The light passed through the tunable filter is coupled to a photo detector (for example a PIN diode for the visible light, or an InGaAs diode for the near infrared light). Photons converted by the photo detector are accumulated as a charge in the integrators. The outputs of the integrators fed into a multiplexed AD converter MUXADC and translated to an electrical signal corresponding to the amount of light detected.

Per substance of interest, a classifier is created beforehand through dimension reduction of the measured spectral range that needs a limited number of data points across the spectrum (typically in the order of 5-20 wavelength bands) to reliably detect the presence and amount of that substance. This is regardless of the type of classifier used. For each substance of interest, the wavelengths to which the filters should be tuned and the spectral coefficients for that wavelength sub range are stored in the memory of the micro controller. The procedure followed by the microcontroller then is:

Tune a filter to the start of the wavelength sub range to be integrated.

Reset the integrator.

Measure and store the accumulated charge in the integrator.

Optionally scan through the whole wavelength sub range if the subrange is larger than the bandwidth of the tunable filter.

Stop measuring and read-out the accumulated charge using the AD converter.

In the microprocessor or microctrontroller MC, calculate the resulting output as a tissue classification by multiplying each measured filter signal with its spectral coefficient from the memory and calculating the final output as the sum of these intermediate filter results. Note that the complexity of the algorithm calculations is reduced to multiplications and additions only, thus meaning that a simple microcontroller (e.g., an ARM-Cortex type) already can provide real-time behavior at a small size and low power consumption. Note that this approach can handle complex classification algorithms based on positive and negative contributions (for example regression vectors). This algorithm uses tunable filters for the specific wavelength ranges where the contribution is non-zero. For a positive contribution, a positive coefficient is used in the calculation, for the negative contribution, a negative coefficient is used. The final summation then combines the positive and negative contributions in a single result.

After that, the next substance can be measured. Dependent on the number of filters in the bank, optionally multiple substances can be measured at the same time, or multiple components of a single substance measured sequentially allowing for a large flexibility with respect to the substances to be classified.

The approach described here can be used in alternative ways:

Full Wavelength Range Spectroscopy implementation with selectable resolution: move a tunable filter across the wavelength range of interest in fixed steps corresponding to the desired resolution and measure the intensity with a photo sensor (e.g., silicon photo diode, InGaAs photo diode, photo multiplier (note that dependent on the detector technology used one or more may be needed to cover the whole wavelength range)). In practice, useful when gathering initial information, or when for example connected to a tablet which executes the more complex algorithms on this information.

Classification algorithms based on ratios. This algorithm uses two or more wavelength bands. A tunable filter is configured for each wavelength band of interest consisting of a band pass filter, photo sensor. The resulting signals can be subtracted and/or divided to provide an indication for the specific characteristic. Measurement speed and accuracy is only limited by the amount of light and the number of bands used. The algorithm is not processor intensive because most of the calculations are done with light in the PIC and only the final division and coefficient multiplication are done in the microcontroller.

Figure 2:
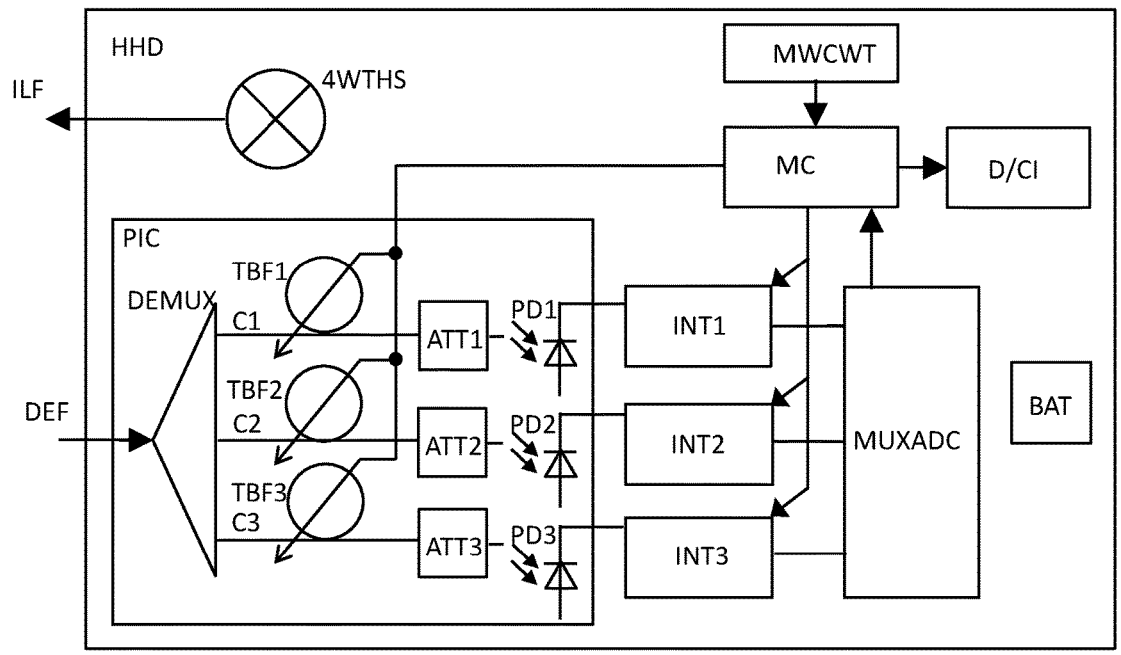
FIG. 2 shows a further embodiment comprising attenuators.

In an alternative embodiment, the amount of calculation required on the microcontroller can be reduced even more by using a more complex PIC which also allows for the configuration of the attenuation, ATT1 . . . ATT3 in FIG. 2, of the filter or allows for a varying tuning speed. This PIC directly implements most of the calculations of a classification algorithm based on positive and negative contributions (for example regression vectors) in the photonic integrated circuit. Each attenuator (ATT1 . . . ATT3 in FIG. 2) may be arranged to digitally modulate the power of the optical signal detected by the photodetector in its optical chain; i.e. to switch it on or off in accordance with the desired spectral coefficient. Alternatively each attenuator may be arranged to apply an analogue amplitude modulation to the power of the optical signal detected by the photodetector in its optical chain, i.e. to apply a spectral coefficient having a value anywhere between and including 0 and 1 to the power of the optical signal detected by the photodetector in its optical chain.

This algorithm uses for example two tunable band filters, two attenuators and two integrating photo sensors. One optical chain containing band filter, attenuator and photo sensor provides the positive contributions to the classification while the other containing its band filter, attenuator and photo sensor provides the negative contributions to the classification. The band filters scan the wavelength range while simultaneously the attenuator is configured with the value of the vector for that specific wavelength. If the contribution is positive, the attenuator in the positive chain is configured with the value, the attenuator in the negative chain is set to zero and vice versa. The end result is the difference between the positive and the negative photo sensor.

Because the two filter chains can be active independently, measurement speed can be increased by only collecting at the relevant wavelengths for the positive/negative contribution, meaning that the positive and the negative chain can operate in parallel, measurement speed can be increased by only collecting at the relevant wavelengths for the positive/ negative contribution, meaning that the positive and the negative chain can operate in parallel.

Alternatively, one can use a single chain and measure the positive and negative contribution sequentially.

Instead of attenuation, one can also vary the time during which signal is integrated in a specific band, or a varying speed at which the band pass filter move across the spectrum with a low speed where there is a high coefficient value of the regression vector and a high speed where there is a low coefficient, and skipping an interval where the coefficient is zero. The algorithm based on the result consists of simple additions/subtractions only and thus is not processor intensive.

Whilst the invention has been illustrated and described in detail in the drawings and foregoing description, such illustrations and description are to be considered illustrative or exemplary and not restrictive; the invention is not limited to the disclosed embodiments and can be used in other applications.

The invention is applicable for important application in healthcare spectral tissue sensing devices. However, this technology will also be beneficial for any other area where spectroscopy is now used such as food inspection, pollution control, crop management, in-vitro diagnostics and analysis of chemical substances.

Summarizing the invention: Spectroscopy has proven to be able to recognize key characteristics of materials such as tissue, food, chemicals et cetera. In specific cases, not the whole spectrum is needed but specific bands in the spectrum are sufficient to characterize a specific substance in the material.

Currently, bulk optics (i.e. discrete optical components) are used which distribute the light per wavelength onto sensors using gratings or prisms. These discrete optical components require a significant amount of space and have a high cost, especially in the near infrared region due to the need for a linear image array of a suitable material such as InGaAs or similar materials. In addition, the full spectral data needs to be collected from such a sensor, thus increasing communication and processing overhead. This conflicts with the need that devices using these technologies are moving towards low-cost, hand-held devices.

With the recent developments of small scale embedded photonics such as photonic integrated circuits, alternative options can be constructed that were not possible without this technology. An example is the ability to integrate multiple tunable narrow-band filters onto a single die. The filters are tunable within milliseconds.

The present invention provides a handheld spectroscopic analysis device HHD (as an add-on to for example a tablet computer, smart phone or smart watch) that uses the tuning of fast tunable filters on a single photonic integrated circuit according to a stored table with wavelengths and spectral coefficients by a simple microcontroller. Calculation of the spectroscopic analysis end result is done with photodetectors such as photodiodes and summation of the resulting signals only, thereby replacing a substantial part of the discrete optical components of such a device and reducing the total amount of data processed.

Due to the tunable characteristics of a filter chain, many different substances can be recognized by applying different filter shapes without requiring changes to the hardware, allowing different applications on the same platform.

Various embodiments of the invention are provided:

1. A spectroscopic analysis device for analysis of a sample comprising:
   an input for receiving light from the sample,
   a photonic integrated circuit comprising one or more tunable bandpass filters arranged to filter the received light, and
   a controller arranged
   to control the one or more tunable bandpass filters,
   to receive filter results obtained from the one or more tunable bandpass filters, and
   to provide spectroscopic analysis results based on the received filter results.

2. A spectroscopic analysis device according to embodiment 1, wherein the photonic integrated circuit comprises one or more photodetectors, each of the photodetectors being operatively connected to a respective one of each of the one or more tunable bandpass filters.

3. A spectroscopic analysis device according to embodiment 2, wherein the photonic integrated circuit comprises one or more attenuators, each of the attenuators being connected between a respective one of each of the one or more tunable bandpass filters and a respective one of the one or more photodetectors.

4. A spectroscopic analysis device according to embodiment 3, wherein the controller is arranged to control the one or more attenuators.

5. A spectroscopic analysis device according to embodiment 1, comprising one or more integrators, whereby each of the one or more integrators is arranged to collect the results from a respective one of the one or more tunable bandpass filters.

6. A spectroscopic analysis device according to embodiment 2, comprising one or more integrators, whereby each of the one or more integrators is connected to a respective one of the one ore photodetectors in order to collect the results from the respective one of the one or more tunable bandpass filters.

7. A spectroscopic analysis device according to embodiment 1, comprising a broadband light source for illuminating the sample.

8. A spectroscopic analysis device according to embodiment 1, comprising a display to display the spectroscopic analysis results.

In an alternative implementation disclosed above and elaborated here in more detail; rather than using a variable attenuator in each optical chain to control the attenuation, attenuation may be effected in the time domain by providing each photodetector in the optical chain with an integrator that is configured to integrate the photodetector's electrical output. Attenuation may be effected by either i) controlling the time that a tunable bandpass filter in each optical chain is arranged to filter a specific wavelength interval or ii) controlling the time during which an integrator is arranged to perform an integration of a specific wavelength interval. Such implementations may be used in a simplified photonic integrated circuit that has no variable attenuator. Since the signal resulting from each integrator depends on both the optical signal intensity detected by the photodetector as well as the time that its corresponding tunable bandpass filter is set to filter a specific wavelength interval, the signal resulting from the integrator may be adjusted through i) and/or ii) above in order to control the contributions of each wavelength interval, i.e. spectral coefficients, to a classification algorithm. For example, if the spectral coefficient of one wavelength interval $\Delta\lambda_1$ is desired to be twice that of another wavelength interval $\Delta\lambda_2$; either the integration time during which the integrator that records the signal at wavelength $\Delta\lambda_1$, or the time during which the tunable bandpass filter is arranged to wavelength interval $\Delta\lambda_1$, may be twice that as for $\Delta\lambda_2$. This form of optical processing by the PIC alleviates the need for separate processing of the results of the contributions of each wavelength interval in a separate controller. This implementation is also compatible with the implementation having a variable attenuator in the PIC; i.e. the control of the integrator and the bandpass filter may be used to perform some parts of the optical processing, and other parts of the optical processing may be performed by a variable attenuator.

The following examples may also be used:

1. A spectroscopic analysis device for analysis of a sample comprising:
   a photonic integrated circuit (PIC) comprising:
   an input (DEF) for receiving light from the sample; and
   a demultiplexer (DEMUX) arranged to distribute the received light into at least a first optical chain (C1) and a second optical chain (C2);
   wherein each optical chain (C1, C2) of the photonic integrated circuit (PIC) further comprises a tunable bandpass filter (TBF1, TBF2) and a photodetector (PD1, PD2) arranged respectively to filter and to detect the light distributed into its corresponding optical chain (C1, C2);
   wherein each optical chain (C1, C2) further comprises an integrator (INT1, INT2) configured to integrate an electrical output of the photodetector in its corresponding optical chain (C1, C2);
   wherein i) each tunable bandpass filter (TBF1, TBF2) is configured to receive control data indicative of a time period ($T_{Filter}$) during which the corresponding tunable bandpass filter (TBF1, TBF2) is arranged to filter a predetermined wavelength interval and/or ii) each integrator (INT1, INT2) is configured to receive control data indicative of a time period ($T_{Int}$) during which the corresponding integrator is arranged to integrate an electrical output of its corresponding photodetector (PD1, PD2), such that the integration result of the corresponding integrator (INT1, INT2) is controlled based on the respective time period ($T_{Filter}$, $T_{Int}$).

2. A spectroscopic analysis device according to example 1 further comprising
   a controller (MC) arranged:
   to control the two or more tunable bandpass filters (TBF1, TBF2),
   to control the two or more integrators (INT1, INT2),
   to receive integrator results obtained from the two or more integrators (INT1, INT2), and
   to provide spectroscopic analysis results based on the received integrator results.

3. A spectroscopic analysis device according to example 2 wherein the controller (MC) further comprises a memory (MWCWT) configured to store a plurality of spectral coefficients indicative of both i) wavelength intervals to be filtered and either ii) time periods ($T_{Filter}$) during which a filter is arranged to filter a predetermined wavelength interval, or iii) time periods ($T_{Int}$) during which an integrator is arranged to integrate an electrical output of its corresponding photodetector (PD1, PD2); and wherein the controller (MC) is further configured to control a result of the integrator (INT1, INT2) in each optical chain (C1, C2) by applying the spectral coefficients to the respective two or more bandpass filters (TBF1, TBF2) or to the respective two or more integrators (INT1, INT2).

4. A spectroscopic analysis device according to any one of examples 2 to 3 wherein the controller (MC) is further arranged to process the received photodetector results based on the difference or the ratio between i) the integrator results received from the integrator of the first optical chain (C1) and ii) the integrator results received from the from the integrator of the second optical chain (C2).

5. A spectroscopic analysis device according to example 2 wherein the controller (MC) is further arranged to control each tunable bandpass filter (TBF1, TBF2) by stepping each tunable bandpass filter (TBF1, TBF2) across a predetermined wavelength range of interest.

6. A spectroscopic analysis device according to example 5 wherein the stepping comprises i) arranging a tunable bandpass filter (TBF1, TBF2) to filter a plurality of wavelength intervals ($\Delta\lambda_1$, $\Delta\lambda_2$) such that a first wavelength interval ($\Delta\lambda_1$) is filtered by the tunable bandpass filter (TBF1, TBF2) during a first time period ($T_{Filter\_1}$) and such that a second wavelength interval ($\Delta\lambda_2$) is filtered by the tunable bandpass filter (TBF1, TBF2) during a second time period ($T_{Filter\_2}$); wherein first time period ($T_{Filter\_1}$) and the second time period ($T_{Filter\_1}$) differ by a factor of at least 1.1; and/or ii) arranging an integrator (INT1, INT2) to integrate an electrical output of its corresponding photodetector (PD1, PD2) such that electrical signals output by the photodetector (PD1, PD2) corresponding to optical wavelengths at a plurality of wavelength intervals ($\Delta\lambda_3$, $\Delta\lambda_4$) are integrated by integrating electrical signals corresponding to optical wavelengths within a third wavelength interval ($\Delta\lambda_3$) during a third time period ($T_{Int\_3}$) and by integrating, with the same integrator (INT1, INT2), electrical signals corresponding to optical wavelengths within a fourth wavelength interval ($\Delta\lambda_4$) during a fourth time period ($T_{Int\_4}$); and wherein the third time period ($T_{Int\_3}$) and the fourth time period ($T_{Int\_4}$) differ by a factor of at least 1.1.

7. A spectroscopic analysis device according to example 2 wherein the controller (MC) is further arranged to control the tunable bandpass filter (TBF1, TBF2) in each optical chain (C1, C2) by setting the tunable bandpass filter (TBF1, TBF2) in each optical chain (C1, C2) to provide an individual optical chain spectral transmission characteristic which when summed together for both optical chains provide a combined spectral transmission characteristic that is coincident with one or more optical emission lines or reflectance bands or absorption bands in a spectrum of the sample.

8. A spectroscopic analysis device according to example 2 wherein the controller (MC) is further arranged to control each tunable bandpass filter (TBF1, TBF2) and each integrator (INT1, INT2) by:
  tuning each filter (TBF1, TBF2) to a start of a wavelength sub-range to be integrated;
  resetting each output of each integrator (INT1, INT2);
  measuring and storing the accumulated charge of the each integrator; and reading-out the accumulated charge of each integrator using an Analogue to Digital converter (MUX-ADC).

9. A spectroscopic analysis device according to example 8 wherein the controller (MC) is further arranged to control each tunable bandpass filter (TBF1, TBF2) by scanning each tunable bandpass filter across a predetermined range of wavelengths starting at the wavelength sub-range.

10. A spectroscopic analysis device according to example 3 wherein the (MC) is further arranged to generate a tissue classification indicative of a tissue type; wherein the tissue classification is generated by:
  multiplying each integrator result by a spectral coefficient stored in the memory of the controller (MWCWT); and
  combining two or more multiplied integrator results through addition, subtraction multiplication or division.

11. A spectroscopic analysis device according to example 1, further comprising a broadband light source (4WTHS) for illuminating the sample.

12. A spectroscopic analysis device according to example 1, comprising a display (D) configured to display the spectroscopic analysis results.

13. A spectroscopic analysis device according to example 1 wherein each tunable bandpass filter (TBF1, TBF2) is an optical ring resonator or a Mach-Zehnder interferometer.

14. A spectroscopic analysis device according to example 1 or example 2 wherein each optical chain (C1, C2) of the photonic integrated circuit (PIC) further comprises a variable attenuator (ATT1, ATT2) arranged to attenuate the light distributed into its corresponding optical chain (C1, C2); wherein the attenuator is disposed between the demultiplexer (DEMUX) and the respective photodetector (PD1, PD2) in each optical chain (C1, C2).

15. Computer program product comprising instructions which when executed on a controller of the spectroscopic analysis device of example 2 cause the controller (MC) to perform the method steps of:
  controlling the two or more tunable bandpass filters (TBF1, TBF2);
  controlling the two or more integrators (INT1, INT2),
  receiving integrator results obtained from the two or more integrators (INT1, INT2); and
  providing spectroscopic analysis results based on the received integrator results;
  wherein the controller (MC) is configured to control the results of the one or more integrators (INT1, INT2) by applying spectral coefficients indicative of i) wavelength intervals to be filtered and either ii) time periods ($T_{Filter}$) during which a filter is arranged to filter a predetermined wavelength interval, or iii) time periods ($T_{Int}$) during which an integrator is arranged to integrate an electrical output of a corresponding photodetector (PD1, PD2).

The invention claimed is:

1. A spectroscopic analysis device for analysis of a sample of a substance based on a classification algorithm having a plurality of spectral coefficients that each correspond to a contribution to the classification algorithm from a wavelength interval, the device comprising:
  an input for receiving light from the sample,
  a photonic integrated circuit comprising:
    one or more tunable bandpass filters arranged to filter the received light, and
    one or more photodetectors;
    wherein each of the photodetectors is operatively connected to a respective one of each of the one or more tunable bandpass filters; and
    wherein each photodetector further comprises an integrator that is configured to integrate an electrical output of the corresponding photodetector, and
  a controller arranged
    to control the one or more tunable bandpass filters,
    to control the one or more integrators;
    to receive, from each integrator, filter results obtained from the one or more tunable bandpass filters,
    wherein the controller is further arranged to provide spectroscopic analysis results of the sample based on the filter results received from each integrator and based on the classification algorithm by either i) attenuating the filtered received light detected by the one or more photodetectors in accordance with the plurality of spectral coefficients by controlling the time during which each tunable bandpass filter filters each wavelength interval or ii) attenuating the integrated signal received from each integrator in accordance with the plurality of spectral coefficients by controlling the time during which each integrator integrates each wavelength interval.

2. A spectroscopic analysis device according to claim 1 further comprising a broadband light source for illuminating the sample.

3. A spectroscopic analysis device according to claim 1 further comprising a display to display the spectroscopic analysis results.

4. A spectroscopic analysis device according to claim 1 further comprising a microcontroller including a memory; wherein the memory is configured to store the plurality of spectral coefficients.

5. A spectroscopic analysis device according to claim 4 having at least two tunable bandpass filters, at least two photodetectors, at least two integrators, and further comprising an analogue to digital converter;
  wherein the analogue to digital converter is connected to the outputs of the at least two integrators and is configured to convert, in a multiplexed manner, the outputs of the at least two integrators into electrical signals that correspond to the amount of light detected by each corresponding photodiode.

6. A method of operating the spectroscopic analysis device of claim 4 comprising the steps of:
  tuning a tunable bandpass filter to a start of a wavelength sub range to be integrated,
  resetting the corresponding integrator,
  measuring and storing an accumulated charge in the integrator, stopping the measuring and reading-out the accumulated charge using the analogue to digital converter, executing a classification algorithm for a sample of a substance by repeating the steps of tuning, resetting, measuring and stopping for each of the plurality of spectral coefficients to generate a plurality of intermediate results, and summing the intermediate results.

* * * * *